United States Patent
Kondo et al.

(10) Patent No.: US 8,178,720 B2
(45) Date of Patent: May 15, 2012

(54) METHOD FOR PRODUCING UNSATURATED ALDEHYDE AND UNSATURATED CARBOXYLIC ACID

(75) Inventors: Masahide Kondo, Hiroshima (JP); Seiichi Kawato, Tokyo (JP); Toru Kuroda, Hiroshima (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 528 days.

(21) Appl. No.: 12/281,694

(22) PCT Filed: Mar. 6, 2007

(86) PCT No.: PCT/JP2007/054245
§ 371 (c)(1),
(2), (4) Date: Jan. 16, 2009

(87) PCT Pub. No.: WO2007/105523
PCT Pub. Date: Sep. 20, 2007

(65) Prior Publication Data
US 2009/0221847 A1  Sep. 3, 2009

(30) Foreign Application Priority Data
Mar. 10, 2006  (JP) .................. 2006-065834

(51) Int. Cl.
C07C 51/00 (2006.01)
C07C 51/16 (2006.01)
(52) U.S. Cl. .................. 562/545; 562/538; 562/532
(58) Field of Classification Search .......... None
See application file for complete search history.

(56) References Cited

U.S. PATENT DOCUMENTS
6,346,646 B1 * 2/2002 Watanabe et al. ............. 562/534

FOREIGN PATENT DOCUMENTS
JP  53-019188  2/1978
(Continued)

OTHER PUBLICATIONS

W.J. Linn, et al., "Oxidation of 1-Butene Over Bismuth Molybdates and Bismuth Iron Molybdate", Journal of Catalysis 41, 134-139 (1976).

(Continued)

Primary Examiner — Karl J Puttlitz
(74) Attorney, Agent, or Firm — Oblon, Spivak, McClelland, Maier & Neustadt, L.L.P.

(57) ABSTRACT

Disclosed is a method of a gas-phase catalytic oxidation reaction of propylene, isobutylene, or tertiary butanol with molecular oxygen in the presence of a catalyst to produce a corresponding unsaturated aldehyde and a corresponding unsaturated carboxylic acid, in which the catalyst can be used over a long period of time. Concretely, in the presence of the catalyst containing a complex oxide including molybdenum, bismuth and iron as essential components, at least one factor of a reaction pressure and a molar ratio of molecular oxygen to a raw material is controlled to change in such a way that a rate of reaction of the raw material is kept constant in the temperature range of from (TA−15)° C. to TA° C., when a boundary temperature of the activation energy of the catalyst is set to be TA° C.

18 Claims, 3 Drawing Sheets

FOREIGN PATENT DOCUMENTS

| | | |
|---|---|---|
| JP | 54-066610 | 5/1979 |
| JP | 55-000359 | 1/1980 |
| JP | 55-019227 | 2/1980 |
| JP | 56-095135 | 8/1981 |
| JP | 60-028824 | 2/1985 |
| JP | 11-263739 | 9/1999 |
| JP | 2001-011010 | 1/2001 |
| JP | 2004-002323 | 1/2004 |

OTHER PUBLICATIONS

S. Kunugi, et al., Arch. Biochem. Biophys., 189, 298 (1978), pp. 178-225 and p. 312.

ISBN4 906317-54-5 C3058, pp. 16-17, Mar. 23, 1995.

* cited by examiner

METHOD FOR PRODUCING UNSATURATED ALDEHYDE AND UNSATURATED CARBOXYLIC ACID

This application is a 371 of PCT/JP2007/054245, filed Mar. 6, 2007.

TECHNICAL FIELD

The present invention relates to a method for producing an unsaturated aldehyde and an unsaturated carboxylic acid, to be more precise, to a method for producing an unsaturated aldehyde and an unsaturated carboxylic acid through gas-phase catalytic oxidation of propylene, isobutylene, or tertiary butanol with molecular oxygen in the presence of a catalyst.

BACKGROUND ART

The method for producing an unsaturated aldehyde and an unsaturated carboxylic acid through gas-phase catalytic oxidation of propylene, isobutylene, or tertiary butanol with molecular oxygen in the presence of a catalyst has been widely known and also has been industrially used. As the catalyst, for example, the one containing a complex oxide including molybdenum, bismuth and iron as essential components is used (Patent Documents 1 to 6). In this case, the reaction is carried out using the catalyst in a fixed-bed at a temperature of 300 to 400° C.

Such a catalyst which is used in a gas-phase catalytic oxidation reaction is used for a relatively long period of time, and usually, activity of the catalyst is lowered and hence a rate of reaction of a raw material is lowered with time. Usually, in a fixed-bed reactor, reaction temperature is raised to an allowable temperature of a process to maintain the rate of reaction of the raw material in response to the activity-lowering with time (Patent Document 7 and Non-Patent Document 1).

Patent Document 1: Japanese Patent Application Laid-Open No. Sho 53-19,188
Patent Document 2: Japanese Patent Application Laid-Open No. Sho 54-66,610
Patent Document 3: Japanese Patent Application Laid-Open No. Sho 55-359
Patent Document 4: Japanese Patent Application Laid-Open No. Sho 55-19,227
Patent Document 5: Japanese Patent Application Laid-Open No. Sho 56-95,135
Patent Document 6: Japanese Patent Application Laid-Open No. Sho 60-28,824
Patent Document 7: Japanese Patent Application Laid-Open No. Hei 11-263,739
Non-Patent Document 1: Yuichi Murakami ed., "Mechanism of Catalyst Degradation and Prevention Method", p. 17, Technical Information Institute Co., Ltd.

DISCLOSURE OF INVENTION

Problem to be Solved by the Invention

However, through the investigation of the present inventors, it is presumed that such controls of temperature only as those described in Patent Document 7 and Non-Patent Document 1 cannot always be sufficiently satisfactory from the viewpoint of industrial practice because speed of activity lowering is relatively fast.

Consequently, it is an object of the present invention to provide a method for producing an unsaturated aldehyde and an unsaturated carboxylic acid, corresponding to polypropylene, isobutylene, or tertiary butanol, through gas-phase catalytic oxidation of the aforementioned propylene, isobutylene, or tertiary butanol with molecular oxygen in the presence of a catalyst, in which the catalyst can be used for a long period of time.

Means for Solving the Problem

The present invention is a method for producing an unsaturated aldehyde and an unsaturated carboxylic acid through gas-phase catalytic oxidation of propylene, isobutylene or tertiary butanol, which is a raw material, with molecular oxygen in the presence of a catalyst comprising a complex oxide including molybdenum, bismuth and iron as essential components, the method comprising:
controlling to change a reaction pressure in such a way that a rate of reaction of the raw material is kept constant in the temperature range of from $(TA-15)°$ C. to $TA°$ C., when a boundary temperature of the activation energy of the catalyst is set to be $TA°$ C.

Further, the present invention is a method for producing an unsaturated aldehyde and an unsaturated carboxylic acid through gas-phase catalytic oxidation of isobutylene or tertiary butanol, which is a raw material, with molecular oxygen in the presence of a catalyst comprising a complex oxide including molybdenum, bismuth and iron as essential components, the method comprising:
controlling to change a molar ratio of oxygen to the raw material in such a way that a rate of reaction of the raw material is kept constant in the temperature range of from $(TA-15)°$ C. to $TA°$ C., when a boundary temperature of the activation energy of the catalyst is set to be $TA°$ C. The method can further comprise controlling to change a reaction pressure.

Effect of the Invention

According to the method for producing an unsaturated aldehyde and an unsaturated carboxylic acid of the present invention, catalyst can be practically used over a long period of time.

BEST MODE FOR CARRYING OUT THE INVENTION

Figure 1:
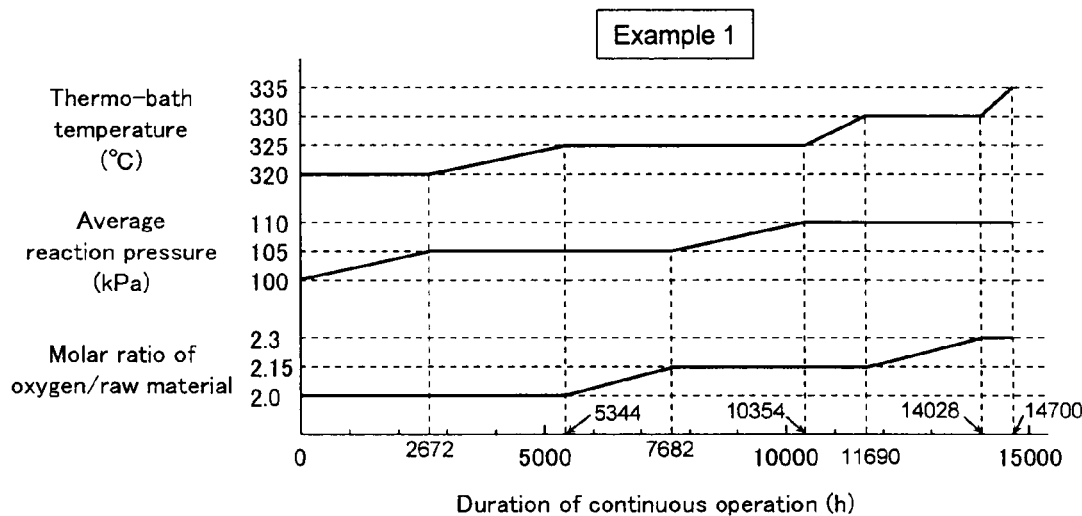
FIG. 1: A diagram showing a control method of the second reaction in Example 1

In the present invention, a catalyst containing a complex oxide including molybdenum, bismuth and iron as essential components is used when propylene, isobutylene or tertiary butanol (hereinafter, expressed also as "TBA") is catalytically oxidized in a gas-phase with molecular oxygen to produce a corresponding unsaturated aldehyde and a corresponding unsaturated carboxylic acid. When propylene is the raw material, the corresponding unsaturated aldehyde and unsaturated carboxylic acid are acrolein and acrylic acid, respectively, and when isobutylene or tertiary butanol is the raw material, the corresponding unsaturated aldehyde and unsaturated carboxylic acid are methacrolein and methacrylic acid, respectively.

The catalyst to be used in the present invention is composed of a complex oxide including molybdenum, bismuth and iron as essential components, and there is no limitation for components other than the essential components in the complex oxide in particular. Such a catalyst can be obtained by publicly known methods such as those described in Patent Documents 1 to 6.

The catalyst to be used in the present invention is preferably the complex oxide that has the composition represented by the following formula (1).

$$Mo_a Bi_b Fe_c M_d X_e Y_f Z_g Si_h O_i \qquad (1)$$

In the formula (1), Mo, Bi, Fe, Si, and O represent molybdenum, bismuth, iron, silicone, and oxygen, respectively. M represents at least one element selected from the group consisting of cobalt and nickel. X represents at least one element selected from the group consisting of chromium, lead, manganese, calcium, magnesium, niobium, silver, barium, tin, tantalum and zinc. Y represents at least one element selected from the group consisting of phosphorus, boron, sulfur, selenium, tellurium, cerium, tungsten, antimony, and titanium. Z represents at least one element selected from the group consisting of lithium, sodium, potassium, rubidium, cesium, and thallium. Each of a, b, c, d, e, f, g, h, and i represents an atomic ratio of each element, respectively, and when a is 12, b is from 0.01 to 3, c is from 0.01 to 5, d is from 1 to 12, e is from 0 to 8, f is from 0 to 5, g is from 0.001 to 2, h is from 0 to 20, and i is the atomic ratio of oxygen that fulfills the requirement of the valence of each component mentioned above.

The complex oxide that is the catalyst to be used in the present invention may be supported on a carrier. As the carrier, silica, alumina, silica-alumina, magnesia, titania, silicon carbide, or the like can be listed.

Hereinafter, a preferable method of production of the catalyst to be used in the present invention will be explained.

As the raw materials of the elements that constitute the catalyst (hereinafter, sometimes abbreviated to "raw materials for catalyst"), though they are not particularly limited, ordinarily, oxides, chlorides, hydroxides, sulfates, nitrates, carbonates, acetates, ammonium salts, or mixtures of these materials can be used. In the case of using chlorides, it is preferable to select candidates from chlorides that can be changed to oxides when ignited. Further, it is possible to use, in particular, metals and sparingly soluble compounds in addition to commonly used water soluble compounds First, a solution or a dispersion liquid (liquid A) that contains at least molybdenum is prepared. In other words, at least a raw material of molybdenum is dissolved or dispersed in a solvent. As the raw material of molybdenum, it is preferable to use ammonium paramolybdate, however, various raw materials such as molybdenum trioxide and molybdenum chloride can also be used. Further, a part or the whole of the raw materials for catalyst corresponding to bismuth, M component, X component, Y component, Z component, and silicon in the case of producing the catalyst represented by the aforementioned formula (1) can be added to the liquid A, in the course of preparing the liquid A or after preparing the liquid A. However, it is preferable not to add a raw material of iron, and hence, it is preferable that the liquid A do not contain iron.

As the solvent of the liquid A, water, alcohol, acetone, or the like can be used. A mixed solvent of two or more kinds of these solvents is also available. It is preferable to use at least water as the solvent, and it is preferable that 50% by mass or more of the whole solvent be water. Further, it is also preferable to use water alone as the solvent.

The mass of the solvent to be used at the time of preparing the liquid A is preferably 70 to 270 parts by mass with respect to 100 parts by mass of the sum of the raw materials for catalyst to be added to the liquid A.

On the other hand, a solution or a dispersion liquid (liquid B) that contains at least iron is prepared. In other words, at least a raw material of iron is dissolved or dispersed in a solvent. As the raw material of iron, ferric nitrate is preferable, however, various raw materials such as iron hydroxide and iron trioxide can also be used. Further, a part or the whole of the raw materials for catalyst corresponding to bismuth, M component, X component, Y component, Z component, and silicon in the case of producing the catalyst represented by the aforementioned formula (1) can be added to the liquid B, in the course of preparing the liquid B or also after preparing the liquid B. However, it is preferable not to add a raw material of molybdenum, and hence, it is preferable that the liquid B do not contain molybdenum.

As the solvent of the liquid B, water, alcohol, acetone, or the like can be used. A mixed solvent of two or more kinds of these solvents is also available. It is preferable to use at least water as the solvent, and it is preferable that 50% by mass or more of the whole solvent be water. Further, it is also preferable to use water alone as the solvent.

The mass of the solvent to be used at the time of preparing the liquid B is preferably to 230 parts by mass with respect to 100 parts by mass of the sum of the raw materials for catalyst to be added to the liquid B.

Subsequently, a solution or a dispersion liquid (liquid C) is prepared by mixing the liquid A and liquid B prepared as mentioned above. Further, a part or the whole of the raw materials for catalyst corresponding to bismuth, M component, X component, Y component, Z component, and silicon in the case of producing the catalyst represented by the aforementioned formula (1) can be added to the liquid C, in the course of preparing the liquid C or also after preparing the liquid C. And thus, liquid D is finally prepared.

The raw materials of bismuth, M component, X component, Y component, Z component, and silicon may be added in such a way that necessary amounts of respective elements are contained in the liquid D finally obtained. Therefore, each raw material for catalyst may be added to any one of the liquid A, liquid B, and liquid C at a time, or may be divided into two or more and added separately to at least one of the liquid A, liquid B, and liquid C at a plurality of times.

The solution or dispersion liquid (liquid D) that contains at least molybdenum, bismuth and iron can be prepared by the methods mentioned above using the necessary raw materials for catalyst. In the case of producing a catalyst in which a complex oxide is supported on a carrier, the carrier may be caused to coexist in the liquid D and the following treatment may be carried out.

Subsequently, it is preferable to hold the obtained liquid D at a temperature in the range of from 80 to 120° C. The holding temperature is more preferably in the temperature range of from 90 to 120° C. When the temperature of the liquid D is held in this temperature range, catalyst performance can be further improved.

The holding time is not particularly limited, however, it is suitably in the range of from 1 second to 30 hours, preferably in the range of from 1 minute to 30 hours, and particularly preferably in the range of from 3 minutes to 15 hours. When the holding time is too short, the effect of improving catalyst performance by holding can hardly be obtained. Further, when the holding time is too long, any additional effect by the prolonged holding can hardly be obtained. The reason for the further improvement of the catalyst performance by the holding is not clear, however, it is presumed that reactivity of the catalyst precursor is improved, so that the catalyst performance is improved.

Subsequently, drying and calcination are carried out when necessary. As the method of drying, various drying methods such as a box type dryer, evaporative drying, and spray drying can be used. The drying condition is preferably 30 to 150° C. in the case of the box type dryer and 100 to 500° C. as an inlet temperature in the case of a spray dryer. Further, as the calcining condition, though it is not particularly limited, a publicly known condition can be adopted. The calcination is usually carried out in the temperature range of from 200 to 600° C. and over the period of from 0.5 to 10 hours. It is preferable to carry out the calcination separately, namely, decomposition of salts and a subsequent calcination.

Subsequently, the obtained catalyst can be molded. The method for molding the catalyst is not particularly limited, and the catalyst can be molded in an optional shape such as spherical shape, ring shape, cylindrical shape, or star shape using a molding machine for general powder such as tablet machine, extruder, or rolling pelletizer.

Further, conventionally known additives, for example, like organic compounds such as polyvinyl alcohol and carboxymethylcellulose may be further added. Further, inorganic compounds such as graphite and diatomaceous earth and inorganic fibers such as glass fiber, ceramic fiber, and carbon fiber may also be added.

The molded catalyst is subjected to heat treatment when necessary. The condition of the heat treatment is not particularly limited, and a publicly known condition for heat treatment can be applied. The heat treatment is usually carried out in the temperature range of from 150 to 600° C. for 0.5 to 80 hours.

As mentioned above, the catalyst composed of a complex oxide including at least molybdenum, bismuth and iron can be obtained.

The catalyst can be used while diluted with an inert substance such as silica, alumina, silica-alumina, magnesia, titania, or silicon carbide.

In the present invention, propylene, isobutylene or tertiary butanol, which is a raw material, is catalytically oxidized in a gas-phase with molecular oxygen in the presence of the aforementioned catalyst to produce a corresponding unsaturated aldehyde and unsaturated carboxylic acid. For example, the gas-phase catalytic oxidation can be carried out by passing a feed gas containing the raw material and molecular oxygen through a reactor packed with the aforementioned catalyst.

As a source of the molecular oxygen, air is economical, however, pure oxygen-enriched air can be used when necessary. The concentration ratio (molar ratio) of the molecular oxygen to the raw material in the feed gas is preferably in the range of from 0.5/1 to 3/1. It is preferable that an inert gas be contained in the feed gas for dilution. The feed gas may contain water vapor. The concentration of the raw material in the feed gas is preferably 1 to 10% by volume.

The reaction pressure is preferably 20 to 300 kPa (gauge pressure; hereinafter, pressure being expressed in gauge pressure) as an average of inlet pressure and outlet pressure of the reaction tube. The reaction temperature can be selected in the range of from 200 to 450° C. The reaction temperature is preferably in the range of from 250 to 400° C. and more preferably in the range of from 310 to 380° C.

However, the activity of such a catalyst that is used in a gas-phase catalytic oxidation declines with time. As the cause of the declination of the activity, there are various theories such as decomposition of catalyst structure by temperature (sublimation or vaporization of catalyst components; change in crystalline phase in catalyst structure), reduction of catalyst components by reactants, and reduction of catalyst components by reactants and temperature. The present inventors have diligently examined these issues and found that the decomposition of catalyst structure by temperature or the reduction of catalyst components by reactants and temperature is the dominative cause of the deterioration of the activity in the present catalyst system, and they have completed the present invention.

Namely, in the present invention, at least one factor of reaction pressure and molar ratio of the molecular oxygen to the raw material (O/R) in the feed gas is controlled to change within the temperature range of from (TA−15)° C. to TA° C. (here, TA (° C.) being a boundary temperature of the activation energy of the catalyst) so as to maintain the rate of reaction of the raw material without raising the reaction temperature as far as possible. By carrying out such a control, the thermal decomposition of catalyst structure or the reduction of catalyst components by reactants and temperature change can be suppressed, and the time of use of the catalyst (catalyst life) is rapidly improved in comparison with the conventional case where only the reaction temperature is controlled. The TA (° C.) can be obtained by the method described in Patent Document 7.

It is known in a gas-phase catalytic reaction using a solid catalyst that the activation energy of the reaction in question often shows different values in each of a low reaction temperature range and high reaction temperature range with a certain reaction temperature being a boundary. For example, it is reported in Journal of Catalysis, Vol. 41, pp 134-139 that such different activation energies as those mentioned above are observed in the catalytic oxidation reaction of 1-butane on a catalyst composed of a composite oxide including molybdenum and bismuth. The reason why such a phenomenon is observed is because the rate-determining step is different depending on the reaction temperature, which is described in detail in Shokubai Koza (Catalysis Course), Vol. 1, Chap. 4, Kodansha Ltd. (edited by Catalysis Society of Japan). According to another opinion, it is presumed that a reaction of reactant molecules on the catalyst active center be the rate-determining step in the low reaction temperature range while diffusion of reactant molecules to the catalyst active center be the rate-determining step in the high reaction temperature range.

The present inventors have analyzed the activation energy of the reaction that produces methacrolein and methacrylic acid through gas-phase catalytic oxidation of isobutylene with molecular oxygen in the presence of a catalyst composed of a complex oxide including molybdenum, bismuth and iron as essential components, and they have confirmed that the activation energy shows different values in each of a low reaction temperature range and high reaction temperature range.

In the present invention, the boundary temperature of the activation energy TA (° C.) can be obtained as follows. First, a catalyst is packed in a reaction tube equipped with Thermo-bath, and the temperature of the Thermo-bath is changed in the range of 315 to 375° C. at an interval of 2 to 5° C., and a rate of reaction of isobutylene is obtained at each temperature. Here, the rate of reaction of isobutylene is obtained by the following equation.

Rate of reaction of isobutylene (%)=$A/B$×100

(A represents number of moles of isobutylene reacted and B represents number of moles of isobutylene supplied.)

$K=(SV)\times(1/\rho)\times\ln[100/(100-X)]$ (K represents reaction rate constant, SV represents space velocity, ρ represents packing density of a catalyst, and X represents rate of reaction (%) of a raw material, respectively.)

Subsequently, 1/T is plotted as horizontal axis and ln K is plotted as vertical axis, and after each datum was plotted, two linear approximation lines were drawn and inclinations of these lines were obtained. Here, 1/T represents the reciprocal of a Thermo-bath temperature (absolute temperature) of the reaction tube and ln K represents a natural logarithm of the reaction rate constant. The linear approximation line can be obtained by a general method such as the least squares method. The absolute value of the inclination of the obtained linear approximation line multiplied by gas constant equals the activation energy to be obtained, and the reciprocal of the value on the horizontal axis of the intersection of the two linear approximation lines is the boundary temperature of the activation energy TA (° C.) to be obtained.

In the case that tertiary butanol is used as the raw material instead of isobutylene, tertiary butanol is immediately decomposed to isobutylene and water in the presence of the catalyst containing molybdenum, bismuth and iron as essential components. In other words, when tertiary butanol is used as the raw material, a reaction scheme is also thought to be essentially same as the oxidation reaction of isobutylene. Therefore, in the case that tertiary butanol is used as the raw material, the same boundary temperature of the activation energy of the reaction of isobutylene can also be used.

In the case that propylene is used as the raw material, the boundary temperature of the activation energy can also be obtained in the same way as in the case of isobutylene.

It is effective to control the reaction pressure so as to rise with the progress of the reaction. The reaction pressure at the start of the reaction is preferably 90 to 110 kPa and more preferably 95 to 105 kPa. The reaction pressure at the end of the reaction is preferably 105 to 125 kPa and more preferably 110 to 120 kPa. The reaction pressure may be raised continuously, however, it is preferably raised stepwise from the viewpoint of easiness of control. When the reaction pressure is raised stepwise, it is preferably raised in two steps or more. When the reaction pressure is raised in two steps, for example, it is preferable to set the first reaction pressure at 95 to 105 kPa, to once set the reaction pressure at 100 to 110 kPa in the middle of the reaction, and to finally set the reaction pressure at 110 to 120 kPa. Here, the reaction pressure means the average of inlet pressure and outlet pressure of the reactor.

It is effective to control the molar ratio of the molecular oxygen to the raw material (O/R) in the feed gas so as to rise with the progress of the reaction. The molar ratio (O/R) at the start of the reaction is preferably 1.8 to 2.2 and more preferably 1.9 to 2.1. The molar ratio (O/R) at the end of the reaction is preferably 2.1 to 2.5 and more preferably 2.2 to 2.4. The molar ratio (O/R) may be raised continuously, however, it is preferably raised stepwise from the viewpoint of easiness of control. When the molar ratio (Q/R) is raised stepwise, it is preferably raised in two steps or more. When the molar ratio (O/R) is raised in two steps, for example, it is preferable to set the first molar ratio (O/R) at 1.95 to 2.05, to once set the molar ratio (O/R) at 2.10 to 2.20 in the middle of the reaction, and to finally set the molar ratio (O/R) at 2.25 to 2.35.

Either the reaction pressure or the molar ratio of the molecular oxygen to the raw material (O/R) in the feed gas may be controlled to change, however, a large effect can be obtained when both the reaction pressure and the molar ratio are controlled to change. When both of them are changed, they may be changed simultaneously or alternately.

When at least one factor of the reaction pressure and the molar ratio of the molecular oxygen to the raw material in the feed gas is changed, the condition may be restored with the elapse of time depending on the extent of the change in the catalyst activity.

The change in at least one factor of the reaction pressure and the molar ratio of the molecular oxygen to the raw material in the feed gas is carried out in such a way that the rate of reaction of the raw material becomes constant. Here, "the rate of reaction of the raw material is constant" means the rate of reaction is within ±2% of the rate of reaction of operation management at the time of normal operation. The rate of reaction of operation management is a target rate of reaction at the time of normal operation. For example, a method in which at least one factor of the reaction pressure and the molar ratio of the molecular oxygen to the raw material in the feed gas is changed, when the rate of reaction of the raw material is lowered to (the rate of reaction of the raw material at the start of the reaction−2%), so as to cause the rate of reaction of the raw material not to exceed (the rate of reaction of the raw material at the start of the reaction+2%) is available.

As mentioned above, TBA is immediately decomposed to isobutylene and water in the presence of the catalyst containing molybdenum, bismuth and iron as essential components. Therefore, the rate of reaction of TBA is calculated regarding isobutylene as the raw material based on the assumption that 100% of TBA is decomposed to isobutylene.

A higher effect can be obtained by controlling to change the reaction temperature in addition to controlling to change at least one factor of the reaction pressure and the molar ratio of the molecular oxygen to the raw material (O/R) in the feed gas.

The production method of the present invention can be used in combination with the activation treatment such as one described in Patent Document 7. Namely, it is possible to carry out activation by holding the catalyst under the temperature in the range of 300° C. or above to less than 550° C. and bringing the catalyst into contact with the gas practically composed of air for 1 hour or more.

The catalyst used in the reaction under the above-mentioned control can also be used further in an ordinary gas-phase catalytic oxidation, and in that case, the time of use of the catalyst (catalyst life) is improved.

EXAMPLES

Hereinafter, the present invention will be explained by examples. In the explanation, "part" means part by mass. The analyses of the reaction products were carried out with gas chromatography. Further, rate of reaction of isobutylene as the raw material and selectivities to methacrolein and methacrylic acid to be produced are defined as follows.

Rate of reaction of the raw material (%)=$A/B$×100

(A represents number of moles of the raw material reacted and B represents number of moles of the raw material supplied.)

Selectivity to methacrolein (%)=$C/A$×100

(A represents number of moles of the raw material reacted and C represents number of moles of methacrolein produced.)

Selectivity to methacrylic acid (%)=D/A×100

(A represents number of moles of the raw material reacted and D represents number of moles of methacrylic acid produced.)

The composition of the catalyst precursor powder other than oxygen was estimated with ICP Atomic Emission Spectrometry and atomic absorption spectrometry of the catalyst precursor powder dissolved in hydrochloric acid.

Reference Example

Catalyst Preparation

To 6,000 parts of water, 3,000 parts of ammonium paramolybdate were dissolved, and then 330.2 parts of antimony trioxide were added while the resultant mixture was stirred, and the resultant mixture was heated to 50° C. to obtain liquid A. Separately, to 5,500 parts of water, 972.5 parts of iron nitrate (III), 3,296.8 parts of cobalt nitrate, 84.3 parts of zinc nitrate, and 110.4 parts of cesium nitrate were dissolved, and to the resultant mixture, a solution obtained by dissolving 150 parts of 60% by mass nitric acid aqueous solution and 480.8 parts of bismuth nitrate in 300 parts of water was added, and the resultant mixture was heated to 30° C. to obtain liquid B.

The liquid B was added to the liquid A while the resultant mixture was stirred to obtain a slurry substance, and the slurry substance was aged at 90° C. for 2 hours, and heated to 103° C. and concentrated for 1 hour, and spray dried to obtain dry powder. The obtained dry powder was calcined at 300° C. for 4 hours to obtain a catalyst precursor powder having the following composition.

$Mo_{12}Bi_{0.7}Fe_{1.7}Co_8Zn_{0.2}Cs_{0.4}Sb_{0.8}O_x$ (In the above formula, MO, Bi, Fe, Co, Zn, Cs, Sb, and O represent molybdenum, bismuth, iron, cobalt, zinc, cesium, antimony, and oxygen, respectively. Further, the numeral written at the right side of each chemical symbol represents an atomic ratio, and x represents the atomic ratio of oxygen that fulfills the requirement of the valence of each component mentioned above.)

With 80 parts of methyl cellulose powder, 3,920 parts of the obtained catalyst precursor powder were mixed, and to the resultant mixture, 1,490 parts of pure water were added, and the resultant mixture was kneaded and molded into ring shape having outer diameter of 5 mm, inner diameter of 2 mm, and height of 5 mm, and the molded article was subjected to heat treatment of 510° C. for 2 hours to obtain a catalyst.

(Determination of the Boundary Temperature of the Activation Energy TA (° C.) of a Catalyst)

To a stainless steel reaction tube which has inside diameter of 27.5 mm and height of 4 m and is equipped with Thermo-bath outside, 2,000 g of the obtained catalyst were packed. Subsequently, a gas-phase catalytic oxidation of isobutylene was carried out under the condition where a feed gas composed of 5% by volume of isobutylene, 12% by volume of oxygen, 10% by volume of water vapor, and 73% by volume of nitrogen was passed through the catalyst layer at a contact time of 3.5 seconds and the temperature of the Thermo-bath was changed in the range of 315 to 375° C. at an interval of 2 to 5° C., and an activation energy was calculated from the rate of reaction of isobutylene at respective temperatures. As a result, the boundary temperature of the activation energy TA (° C.) was 335° C., and the activation energy of the lower temperature side of the boundary temperature was 100 kJ/mol, and that of higher temperature side was 32 kJ/mol. The average reaction pressure was 98 kPa.

Example 1

The First Reaction

To the reaction tube used in the Reference Example, 2,000 g of the catalyst obtained in the Reference Example was packed. Subsequently, the temperature of the Thermo-bath was set to 320° C., and a gas-phase catalytic oxidation of isobutylene was carried out under the condition where a feed gas composed of 5% by volume of isobutylene (the raw material of the reaction), 9% by volume of oxygen, 10% by volume of water vapor, and 76% by volume of nitrogen was passed through the catalyst layer at a contact time of 4.5 seconds. As a result of analyzing the reaction products in an early stage, the rate of reaction of isobutylene was 95.7%, the selectivity to methacrolein was 87.9%, and the selectivity to methacrylic acid was 5.4%. At this stage, the temperature of the Thermo-bath was 320° C., the average reaction pressure was 100 kPa, and the molar ratio of the molecular oxygen to the raw material in the feed gas was 2.0 (initial reaction condition).

The Second Reaction

Following the first reaction, control was carried out with the rate of reaction of operation management being 95%. Concretely, the temperature of the Thermo-bath, the average reaction pressure, and the molar ratio of the molecular oxygen to the raw material in the feed gas were changed as shown in FIG. 1. The duration of continuous operation became 14,700 hours. As a result of analyzing the reaction products at this stage, the rate of reaction of isobutylene was 95.7%, the selectivity to methacrolein was 87.8%, and the selectivity to methacrylic acid was 5.3%. At this stage, the temperature of the Thermo-bath was 335° C., the average reaction pressure was 110 kPa, and the molar ratio of the molecular oxygen to the raw material in the feed gas was 2.3 (reaction condition 1).

The Third Reaction

Following the second reaction, the reaction was once stopped, and resumed with the initial reaction condition. As a result of analyzing the reaction products in an early stage of the resumed reaction, the rate of reaction of isobutylene was 93.5%, the selectivity to methacrolein was 87.7%, and the selectivity to methacrylic acid was 5.3%.

The Fourth Reaction

Following the third reaction, the reaction condition was changed to the reaction condition 1, and the reaction was continued till the temperature of the Thermo-bath became 360° C. while the temperature of the Thermo-bath was controlled to rise in such a way that the rate of reaction of isobutylene became constant. The duration of continuous operation became 19,200 hours in all. As a result of analyzing the reaction products at this stage, the rate of reaction of isobutylene was 95.7%, the selectivity to methacrolein was 87.6%, and the selectivity to methacrylic acid was 5.3%.

Example 2

The First Reaction

The first reaction was carried out in the same manner as in Example 1.

The Second Reaction

Figure 2:
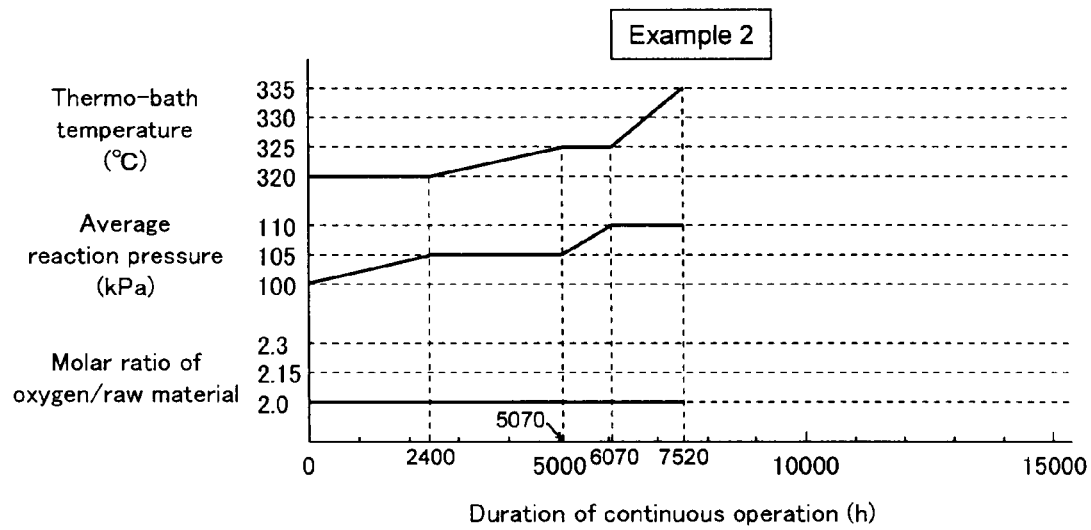
FIG. 2: A diagram showing a control method of the second reaction in Example 2

Following the first reaction, the second reaction was carried out in the same manner as in Example 1 except that the temperature of the Thermo-bath and the average reaction pressure were changed as shown in FIG. 2. The duration of continuous operation became 7,520 hours. As a result of analyzing the reaction products at this stage, the rate of reaction of isobutylene was 95.6%, the selectivity to methacrolein was 87.9%, and the selectivity to methacrylic acid was 5.4%. At this stage, the temperature of the Thermo-bath was 335° C., the average reaction pressure was 110 kPa, and the molar ratio of the molecular oxygen to the raw material in the feed gas was 2.0 (reaction condition 2).

The Third Reaction

Following the second reaction, the third reaction was carried out in the same manner as in Example 1. As a result of analyzing the reaction products in an early stage of the resumed reaction, the rate of reaction of isobutylene was 93.4%, the selectivity to methacrolein was 87.8%, and the selectivity to methacrylic acid was 5.4%.

The Fourth Reaction

Following the third reaction, the fourth reaction was carried out in the same manner as in Example 1 except that the reaction condition was changed to the reaction condition 2, and the reaction was continued till the temperature of the Thermo-bath became 360° C. The duration of continuous operation became 14,400 hours in all. As a result of analyzing the reaction products at this stage, the rate of reaction of isobutylene was 95.6%, the selectivity to methacrolein was 87.7%, and the selectivity to methacrylic acid was 5.4%.

Example 3

The First Reaction

The first reaction was carried out in the same manner as in Example 1.

The Second Reaction

Figure 3:
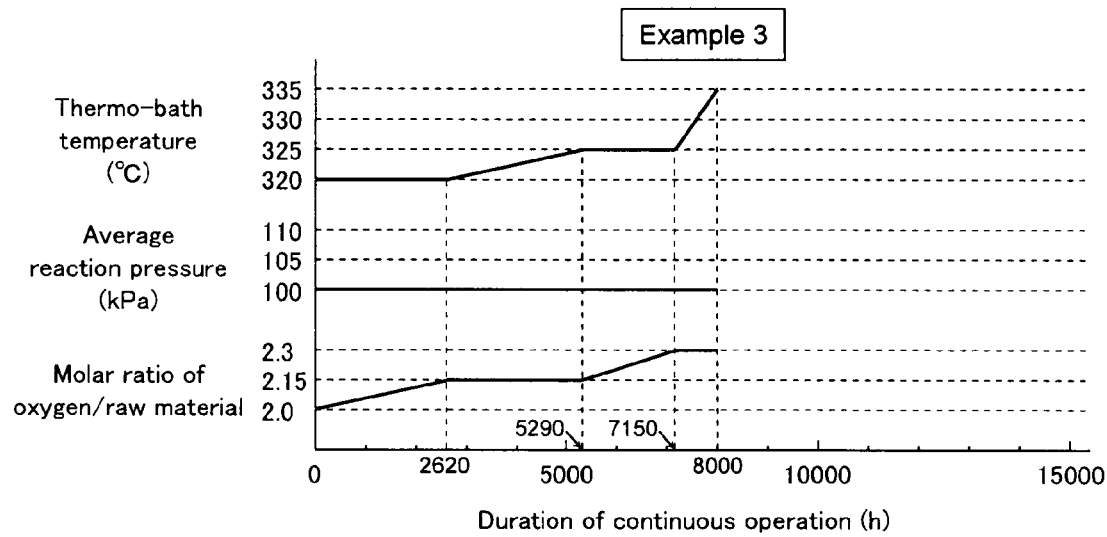
FIG. 3: A diagram showing a control method of the second reaction in Example 3

Following the first reaction, the second reaction was carried out in the same manner as in Example 1 except that the temperature of the Thermo-bath and the molar ratio of the molecular oxygen to the raw material in the feed gas were changed as shown in FIG. 3. The duration of continuous operation became 8,000 hours. As a result of analyzing the reaction products at this stage, the rate of reaction of isobutylene was 95.7%, the selectivity to methacrolein was 87.9%, and the selectivity to methacrylic acid was 5.4%. At this stage, the temperature of the Thermo-bath was 335° C., the average reaction pressure was 100 kPa, and the molar ratio of the molecular oxygen to the raw material in the feed gas was 2.3 (reaction condition 3).

The Third Reaction

Following the second reaction, the third reaction was carried out in the same manner as in Example 1. As a result of analyzing the reaction products in an early stage of the resumed reaction, the rate of reaction of isobutylene was 93.5%, the selectivity to methacrolein was 87.9%, and the selectivity to methacrylic acid was 5.4%.

The Fourth Reaction

Following the third reaction, the fourth reaction was carried out in the same manner as in Example 1 except that the reaction condition was changed to the reaction condition 3, and the reaction was continued till the temperature of the Thermo-bath became 360° C. The duration of continuous operation became 15,000 hours in all. As a result of analyzing the reaction products at this stage, the rate of reaction of isobutylene was 95.7%, the selectivity to methacrolein was 87.7%, and the selectivity to methacrylic acid was 5.4%.

Example 4

Figure 4:
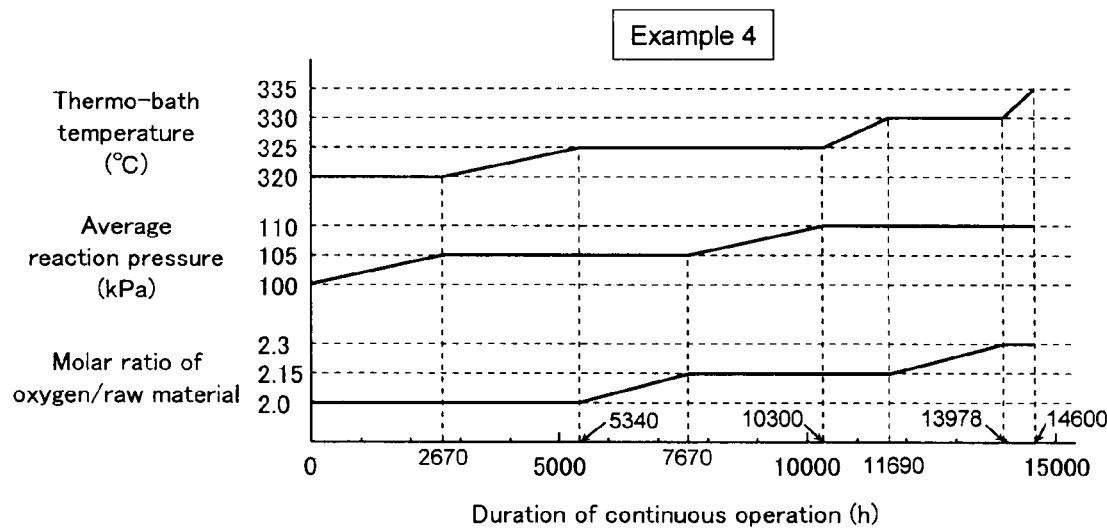
FIG. 4: A diagram showing a control method of the second reaction in Example 4

The reaction was carried out in the same manner as in Example 1 except that tertiary butanol (TBA) was used as the raw material instead of isobutylene, and the temperature of the Thermo-bath, the average reaction pressure, and the molar ratio of the molecular oxygen to the raw material in the feed gas were changed as shown in FIG. 4 in the second reaction. The rate of reaction of TBA is calculated regarding isobutylene as the raw material based on the assumption that 100% of TBA is decomposed to isobutylene.

As a result, the duration of continuous operation of the second reaction became 14,600 hours, and the duration of continuous operation through the fourth reaction became 19,100 hours.

Comparative Example 1

The First Reaction

The first reaction was carried out in the same manner as in Example 1.

Figure 5:
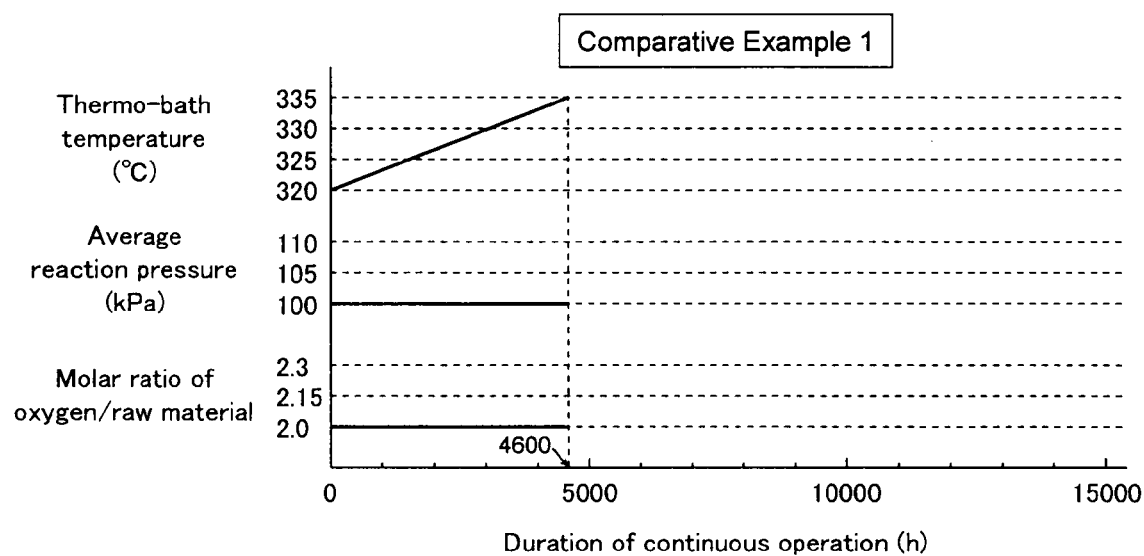
FIG. 5: A diagram showing a control method of the second reaction in Comparative Example 1

Following the first reaction, the second reaction was carried out in the same manner as in Example 1 except that the temperature of the Thermo-bath was changed as shown in FIG. 5. The duration of continuous operation became 4,600 hours. As a result of analyzing the reaction products at this stage, the rate of reaction of isobutylene was 95.4%, the selectivity to methacrolein was 88.0%, and the selectivity to methacrylic acid was 5.5%. At this stage, the temperature of the Thermo-bath was 335° C., the average reaction pressure was 100 kPa, and the molar ratio of the molecular oxygen to the raw material in the feed gas was 2.0 (reaction condition 4).

TABLE 1

| | Raw material | Control in the second reaction | | | Duration of continuous operation in the second reaction | Duration of continuous operation through the fourth reaction |
| | | Average reaction pressure | Molar ratio of Oxygen to raw material | Temperature of Thermo-bath | | |
| --- | --- | --- | --- | --- | --- | --- |
| Ex. 1 | isobutylene | ◯ | ◯ | ◯ | 14,700 hours | 19,200 hours |
| Ex. 2 | isobutylene | ◯ | | ◯ | 7,520 hours | 14,400 hours |
| Ex. 3 | isobutylene | | ◯ | ◯ | 8,000 hours | 15,000 hours |

TABLE 1-continued

| | | Control in the second reaction | | | Duration of | Duration of |
| | Raw material | Average reaction pressure | Molar ratio of Oxygen to raw material | Temperature of Thermo-bath | continuous operation in the second reaction | continuous operation through the fourth reaction |
|---|---|---|---|---|---|---|
| Ex. 4 | TBA | ○ | ○ | ○ | 14,600 hours | 19,100 hours |
| Comp. Ex. 1 | isobutylene | | | ○ | 4,600 hours | — |

What is claimed is:

1. A method for producing an unsaturated aldehyde and an unsaturated carboxylic acid through gas-phase catalytic oxidation of propylene, isobutylene or tertiary butanol, which is a raw material, with molecular oxygen in the presence of a catalyst comprising a complex oxide including molybdenum, bismuth and iron as essential components, the method comprising:
controlling reaction pressure in such a way that a rate of reaction of the raw material is kept constant in the temperature range of from $(TA-15)°$ C. to $TA°$ C., where $TA°$ C. is the boundary temperature of the activation energy of the catalyst, and
controlling reaction pressure such that the reaction pressure rises with the progress of the reaction of the raw material, wherein
the reaction pressure at the start of the reaction is 90 to 110 kPa and is 105 to 125 kPa at the end of the reaction, where reaction pressure is an average of inlet pressure and outlet pressure and is expressed in gauge pressure.

2. The method as claimed in claim 1, comprising controlling reaction pressure and the molar ratio of oxygen to the raw material in such a way that a rate of reaction of the raw material is kept constant in the temperature range of from $(TA-15)°$ C. to $TA°$ C.

3. The method as claimed in claim 1, wherein said method is a method for producing an unsaturated aldehyde and an unsaturated carboxylic acid through gas-phase catalytic oxidation of propylene with molecular oxygen.

4. The method as claimed in claim 1, wherein said method is a method for producing an unsaturated aldehyde and an unsaturated carboxylic acid through gas-phase catalytic oxidation of isobutylene with molecular oxygen.

5. The method as claimed in claim 1, wherein said method is a method for producing an unsaturated aldehyde and an unsaturated carboxylic acid through gas-phase catalytic oxidation of tertiary butanol with molecular oxygen.

6. The method as claimed in claim 2, wherein said method is a method for producing an unsaturated aldehyde and an unsaturated carboxylic acid through gas-phase catalytic oxidation of propylene with molecular oxygen.

7. The method as claimed in claim 2, wherein said method is a method for producing an unsaturated aldehyde and an unsaturated carboxylic acid through gas-phase catalytic oxidation of isobutylene with molecular oxygen.

8. The method as claimed in claim 2, wherein said method is a method for producing an unsaturated aldehyde and an unsaturated carboxylic acid through gas-phase catalytic oxidation of tertiary butanol with molecular oxygen.

9. The method as claimed in claim 1, wherein said catalyst is represented by the following formula (I):

$$Mo_aBi_bFe_cM_dX_eY_fZ_gSi_hO_i \quad (I)$$

wherein M represents at least one element selected from the group consisting of cobalt and nickel, X represents at least one element selected from the group consisting of chromium, lead, manganese, calcium, magnesium, niobium, silver, barium, tin, tantalum and zinc, Y represents at least one element selected from the group consisting of phosphorus, boron, sulfur, selenium, tellurium, cerium, tungsten, antimony, and titanium, Z represents at least one element selected from the group consisting of lithium, sodium, potassium, rubidium, cesium, and thallium, a is 12, b is from 0.01 to 3, c is from 0.01 to 5, d is from 1 to 12, e is from 0 to 8, f is from 0 to 5, g is from 0.001 to 2, h is from 0 to 20, and i is the atomic ratio of oxygen that fulfills the requirement of the valence of each component.

10. The method as claimed in claim 9, comprising controlling reaction pressure and the molar ratio of oxygen to the raw material in such a way that a rate of reaction of the raw material is kept constant in the temperature range of from $(TA-15)°$ C. to $TA°$ C.

11. The method as claimed in claim 9, wherein said method is a method for producing an unsaturated aldehyde and an unsaturated carboxylic acid through gas-phase catalytic oxidation of propylene with molecular oxygen.

12. The method as claimed in claim 9, wherein said method is a method for producing an unsaturated aldehyde and an unsaturated carboxylic acid through gas-phase catalytic oxidation of isobutylene with molecular oxygen.

13. The method as claimed in claim 9, wherein said method is a method for producing an unsaturated aldehyde and an unsaturated carboxylic acid through gas-phase catalytic oxidation of tertiary butanol with molecular oxygen.

14. The method as claimed in claim 1, wherein the reaction pressure at the start of the reaction is 95 to 105 kPa and is 110 to 120 kPa at the end of the reaction.

15. The method as claimed in claim 1, wherein the reaction pressure rises continuously with the progress of the reaction of the raw material.

16. The method as claimed in claim 1, wherein the reaction pressure rises stepwise with the progress of the reaction of the raw material.

17. The method as claimed in claim 16, wherein the reaction pressure rises in two steps or more.

18. The method as claimed in claim 17, wherein the reaction pressure rises in two steps, wherein a first reaction pressure is set at 95 to 105 kPa, a middle reaction pressure is set at 100 to 110 kPa, and a final reaction pressure is set at 110 to 120 kPa.

* * * * *